(12) United States Patent
Ito et al.

(10) Patent No.: US 6,879,788 B2
(45) Date of Patent: Apr. 12, 2005

(54) IMAGE FORMING APPARATUS WITH DENSITY DETECTING MEANS

(75) Inventors: Nobuyuki Ito, Shizuoka (JP); Takeshi Ikeda, Shizuoka (JP); Yukio Nagase, Shizuoka (JP); Isami Itoh, Shizuoka (JP); Yasukazu Ayaki, Kanagawa (JP); Tomohito Ishida, Shizuoka (JP)

(73) Assignee: Canon Kabushiki Kaisha, Tokyo (JP)

( * ) Notice: Subject to any disclaimer, the term of this patent is extended or adjusted under 35 U.S.C. 154(b) by 22 days.

(21) Appl. No.: 10/648,318

(22) Filed: Aug. 27, 2003

(65) Prior Publication Data

US 2004/0096232 A1 May 20, 2004

(30) Foreign Application Priority Data

Aug. 29, 2002 (JP) .......................................... 2002-251111

(51) Int. Cl.⁷ .............................................. G03G 15/00
(52) U.S. Cl. ....................................................... 399/49
(58) Field of Search .......................... 399/49, 223, 252; 430/45, 106, 137

(56) References Cited

U.S. PATENT DOCUMENTS

| 6,013,403 A | 1/2000 | Ichikawa | ..................... 430/97 |
|---|---|---|---|
| 6,120,959 A * | 9/2000 | Sugizaki et al. | ......... 430/108.9 |
| 6,327,450 B1 | 12/2001 | Ito | .............................. 399/227 |
| 6,498,910 B2 | 12/2002 | Haneda | ....................... 399/51 |

FOREIGN PATENT DOCUMENTS

| JP | 58-39468 | | 3/1983 |
|---|---|---|---|
| JP | 11-084764 | * | 3/1999 |
| JP | 2000-122359 | | 4/2000 |
| JP | 2000-231279 | | 8/2000 |
| JP | 2000-305339 | | 11/2000 |
| JP | 2000-347476 | | 12/2000 |
| JP | 2001-290319 | | 10/2001 |
| JP | 2002-144250 | | 5/2002 |

* cited by examiner

*Primary Examiner*—Hoang Ngo
(74) *Attorney, Agent, or Firm*—Fitzpatrick, Cella, Harper & Scinto

(57) ABSTRACT

The image forming apparatus includes an image forming unit capable of forming an image with a hypochromic toner and a hyperchromic toner of a substantially same hue, a first toner containing portion containing the hypochromic toner, a second toner containing portion containing the hyperchromic toner, and a density detecting unit which detects a density of an image formed with the hypochromic toner and the hyperchromic toner. Thus an image can be formed with the hypochromic toner and the hyperchromic toner of a substantially same hue.

27 Claims, 15 Drawing Sheets

IMAGE FORMING APPARATUS WITH DENSITY DETECTING MEANS

BACKGROUND OF THE INVENTION

1. Field of the Invention

The present invention relates to an image forming apparatus such as a copying apparatus, a printer or a facsimile apparatus for image formation with hyperchromic toner and hypochromic toner.

2. Related Background Art

As an image forming apparatus for forming a color image, there is already commercialized an image forming apparatus capable of transferring color images by precisely superimposing succession toner images of respective colors, formed on a photosensitive drum serving as an image bearing member, onto a transfer material such as paper supported for example on a transfer drum (transfer film), thereby forming a color image.

In such image forming apparatus, an electrostatic latent image, formed on the photosensitive drum according to an input image signal, is developed with toner of a first color (for example cyan color) to obtain a toner image, which is transferred onto a transfer material such as paper supported on a transfer drum (transfer film). Such transfer process is repeated similarly for other three colors, namely magenta, yellow and black, whereby a color image is obtained by superposed transfers of toner images of four colors on the transfer material.

In the recent electrophotographic image forming apparatus utilizing digital image signals, the latent image is formed by a group of dots of a constant potential on the surface of an image bearing member or so-called photosensitive member, and a solid image portion, a halftone image portion and a line image portion are obtained by changing the density of the dots.

In such method, however, toner particles cannot faithfully be deposited on the dot but tend to overflow from the dot, whereby the gradation of the toner image does not correspond to a ratio of the dot densities in a black portion and a white portion of the digital latent image.

Also in case of increasing the resolution by reducing the dot size in order to improve the image quality, the latent image constituted of finer dots becomes more difficult to reproduce thereby leading to an image lacking sharpness and poor in the resolution and the gradation particularly in the highlight portion. Also an irregular arrangement in the dot is observed as a granularity and deteriorates the image quality particularly in the highlight portion.

Such irregularity is not present in the ink jet recording or in the lithographic printing, and is an unpredictable factor in the image quality and causes a macroscopic low-frequency noise generated by a random distribution of small toner particles of a size of 5 to 10 $\mu$m along the dot contour.

A magnified observation of an electrophotographic image reveals that a dot formed by an electrophotographic process does not have a smooth contour as in ink jet recording but is formed by a random distribution of the small toner particles of a size of 5 to 10 $\mu$m along the dot contour. Also such dots are not uniformly formed but are uneven, with low density ones and high density ones, also with those of smaller and larger diameters and with non-circular shapes. These factors show almost random fluctuation and include considerable low-frequency components, which lead, as a result, to a visible noise.

Such noise is rendered conspicuous particularly by a difference in the density of the toner and that of the paper. Particularly in comparison with the ink jet recording, there results a significant influence of an optical dot gain, resulting from a distribution of a large number of small toner particles.

These phenomena are principally generated by a fact that small toner particles are used for the dot formation in the electrophotographic process. Also there are various subsidiary factors such as an unsharpening of dot data in the electrophotographic process involving steps of latent image formation, image development and image transfer, an irregular toner scattering resulting from physical properties (electrical resistance, surface roughness) of the copying paper, and a phenomenon resulting from an adhesion force in the development process to be explained in the following.

There is a strong adhesion force (principally a mirror force of toner to a developer bearing member) between the toner and the developing sleeve in case of a single-component developer or between the toner and the carrier in case of a two-component developer, while the toner particles have uneven distribution of charge. Therefore, in peeling off such toner particles with a developing bias voltage to cause a flight toward the photosensitive drum, image formation becomes uneven as the toner particles in a part can easily fly while those in another part do not fly so easily, whereby formation of the dots becomes uneven.

On the other hand, a hyperchromic-hypochromic ink process in the ink jet recording as disclosed in Japanese Patent Application Laid-Open No. 58-39468 is free from the above-mentioned drawbacks the electrophotographic process because the ink jet system is simpler and the high image quality is supported by current paper exclusive for ink jet recording.

Based on an effect of improving the granularity by the hyperchromic and hypochromic inks employed for example in the ink jet recording, it is found that the use of a hypochromic toner in the electrophotographic process is far effective than in the ink jet recording in reducing the visible low-frequency noise, resulting from "a fluctuation in the toner density constituting the dot", "a fluctuation in the dot area", and "a fluctuation in the dot shape".

It is also found that the introduction of the hypochromic toner in the electrophotographic process brings about a revolutionary progress in reducing the optical dot grain which is not a problem in the ink jet recording but has been a serious problem in attaining a high image quality in the electrophotographic process based on a multitude of small toner particles.

For avoiding these drawbacks, there is already proposed a method of employing a pale-colored toner (hypochromic toner) in a highlight area and a dense-colored toner (hyperchromic toner) in a solid image area. Japanese Patent Applications Laid-Open Nos. H11-84764 and 2000-305339 refer to an image forming method for forming an image by combining plural toners of different densities. Also Japanese Patent Application Laid-Open No. 2000-347476 refers to an image forming apparatus employing a combination of a hyperchromic toner and a hypochromic toner of a maximum reflective density less than a half of the maximum reflective density of the hyperchromic toner. Also Japanese Patent Application Laid-Open No. 2000-231279 refers to an image forming apparatus employing a combination of a hyperchromic toner having an image density of 1.0 or higher at a toner amount of 0.5 mg/cm$^2$ on a transfer material and a hypochromic toner having an image density less than 1.0. Also Japanese Patent Application Laid-Open No. 2001-290319 refers to an image forming apparatus employing a hyperchromic toner and a hypochromic toner having an inclination ration of the recording density within a range from 0.2 to 0.5.

However, such prior technologies as explained above have been associated with following drawbacks.

Investigation of the present inventors has revealed that, in such technologies, the gradation and the granularity are improved in a low-density area constituted solely of the hypochromic toner, but the granularity becomes more evident in a medium-density area where the hyperchromic toner and the hypochromic toner are mixedly present.

This is caused by a fact that a state in which the hyperchromic toner is present in a very small amount in the hypochromic toner is extremely unstable in the process condition but is very sensitive visually.

Such instability, which has been avoided in the prior ink jet printer employing six-colored inks (hyperchromic and hypochromic inks) by delicately controlling the ink discharge amount, is in fact the reason why such hyperchromic-hypochromic system has not been adopted in the electrophotographic apparatus.

SUMMARY OF THE INVENTION

An object of the present invention is to provide an image forming apparatus capable of forming an image with a hypochromic toner and a hyperchromic toner of substantially same colors.

Another object of the present invention is to provide an image forming apparatus capable of providing an excellent gradation in a highlight area.

Another object of the present invention is to provide an image forming apparatus capable of avoiding granularity even in a medium-density area where the hypochromic toner and the hyperchromic toner are mixedly presented.

Another object of the present invention is to provide an image forming apparatus capable of providing a satisfactory image over the entire gradation range.

Still other objects of the present invention, and the advantages thereof, will become fully apparent from the following description, which is to be taken in conjunction with the accompanying drawings.

DETAILED DESCRIPTION OF THE PREFERRED EMBODIMENTS

In the following the present invention will be clarified by examples of preferred embodiments thereof with reference to accompanying drawings, but dimensions, materials, shapes, relative positions etc. of components described in these embodiments are not to limit the scope of the present invention unless specified otherwise.

(First Embodiment)

Figure 1:
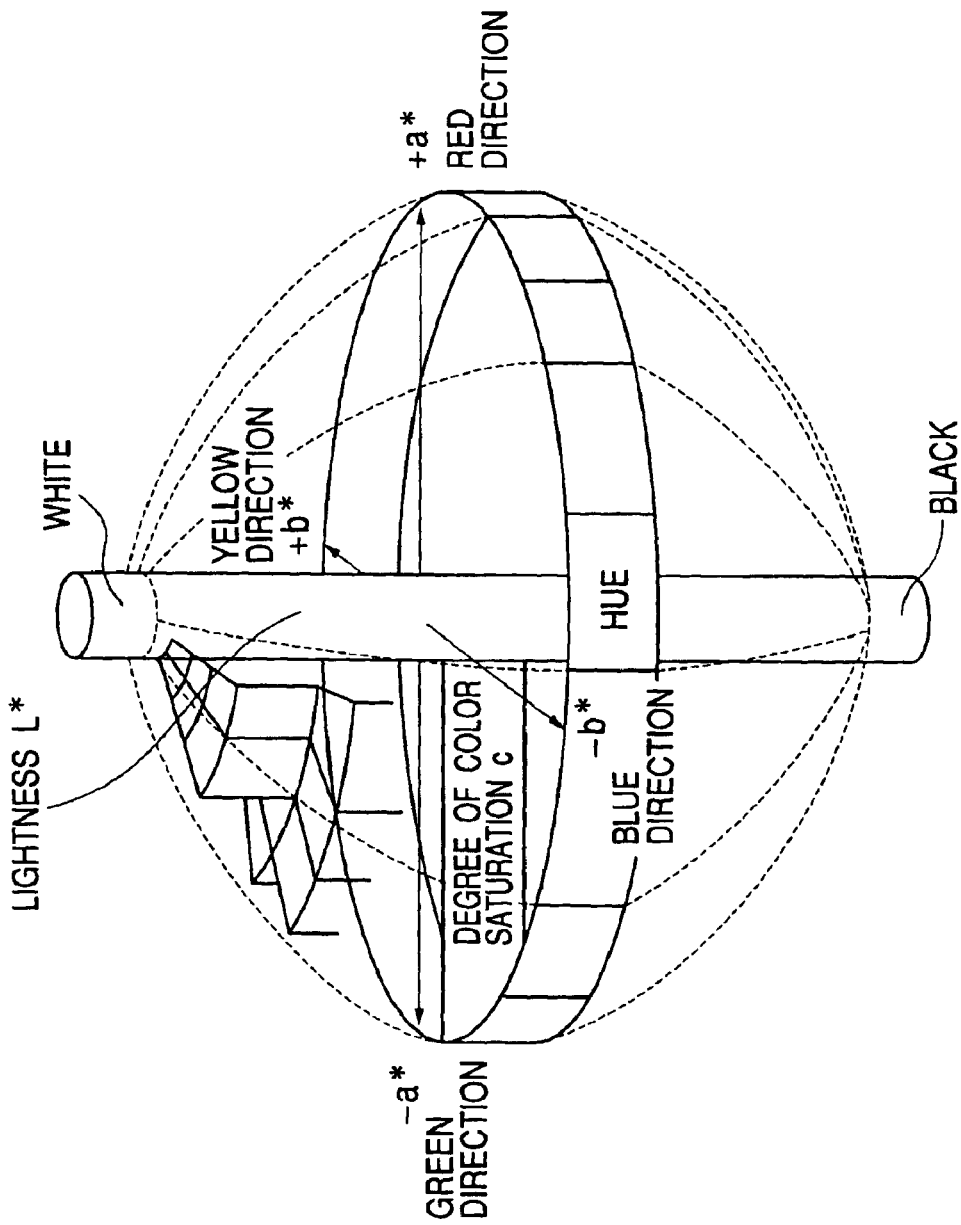
FIG. 1 is a conceptual view of a color solid of a L*a*b* color presenting system employed in embodiments of the present invention.

In the present embodiment, L* is a value commonly employed as the L*a*b* color presentation system and is effective means for indicating a color by a number. A solid concept of such system is shown in FIG. 1. In FIG. 1, horizontal axes a* and b* in combination represent hues, which represent various colors such as red, yellow, green, blue, violet etc. A vertical axis L* represents a lightness (luminocity), indicating luminance of color, comparable regardless of the hue. The axes a* and b* indicate color directions, respectively in red-green and in yellow-blue.

Figure 2:
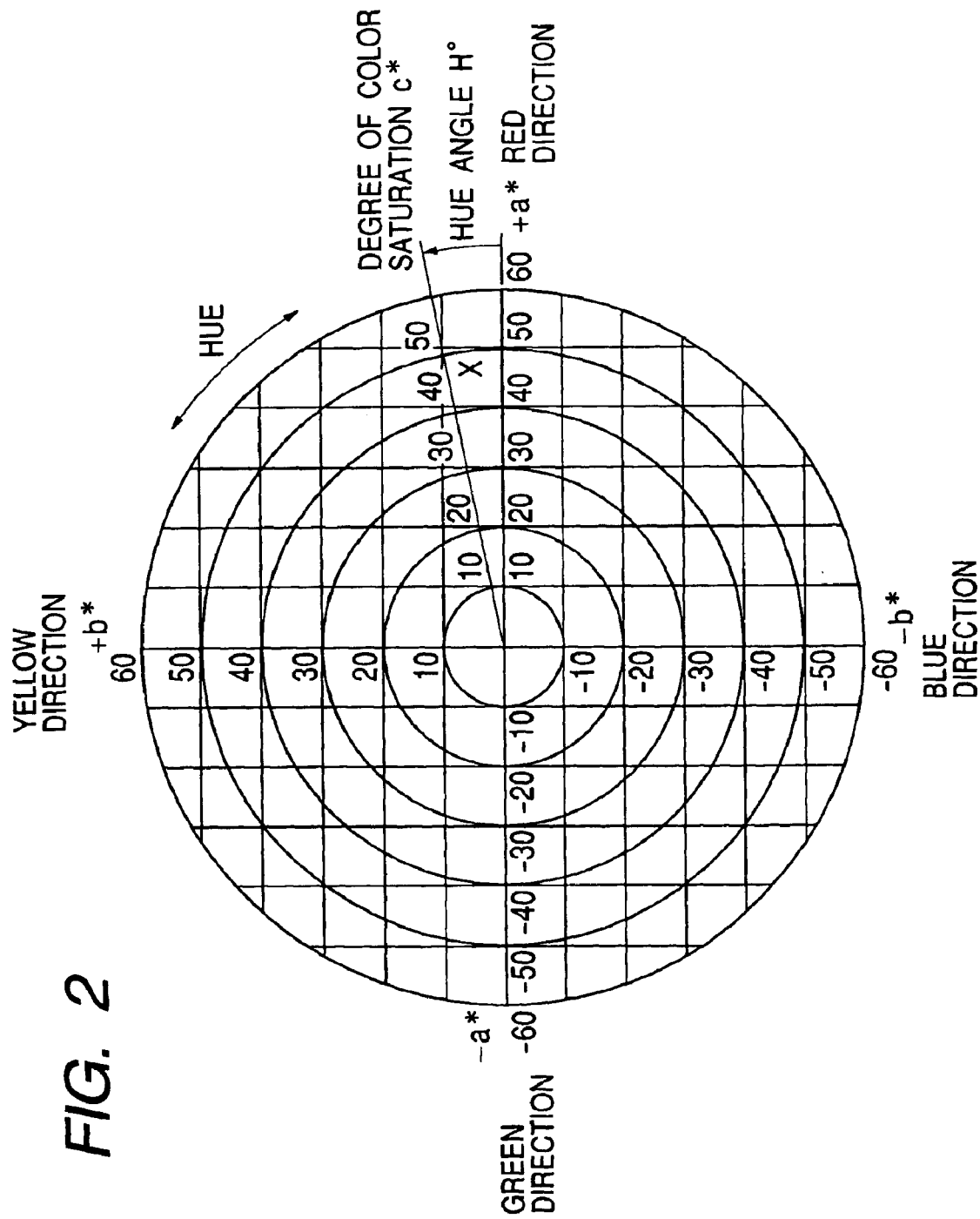
FIG. 2 is a conceptual planar view of hue-chromaticity, and hue angle employed in embodiments.

FIG. 2 is a planar chart showing a hue-chromaticity relationship at a certain luminocity. In this chart, c* represents color saturation (chromaticity), determined by a following equation (1) and indicating a level of saturation of color:

$$c^* = \sqrt{(a^{*2}+b^{*2})} \tag{1}$$

Also a hue angle H means, for a color positioned at a point X(a*, b*) on the a*-b* coordinate system, an angle of a line connecting the point X(a*, b*) and the original point in a counterclockwise direction from the plus-side of the a* axis. The hue angle can easily represent a specified hue independently from the lumonocity.

Figure 3:
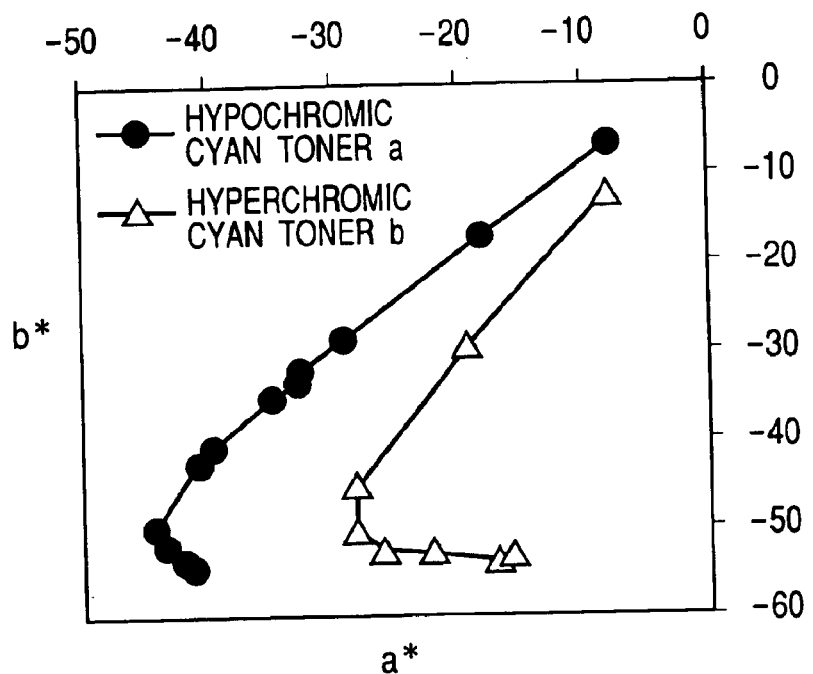
FIG. 3 is a chart showing an example of a hue curve of toners embodying the present invention.
Figure 4:
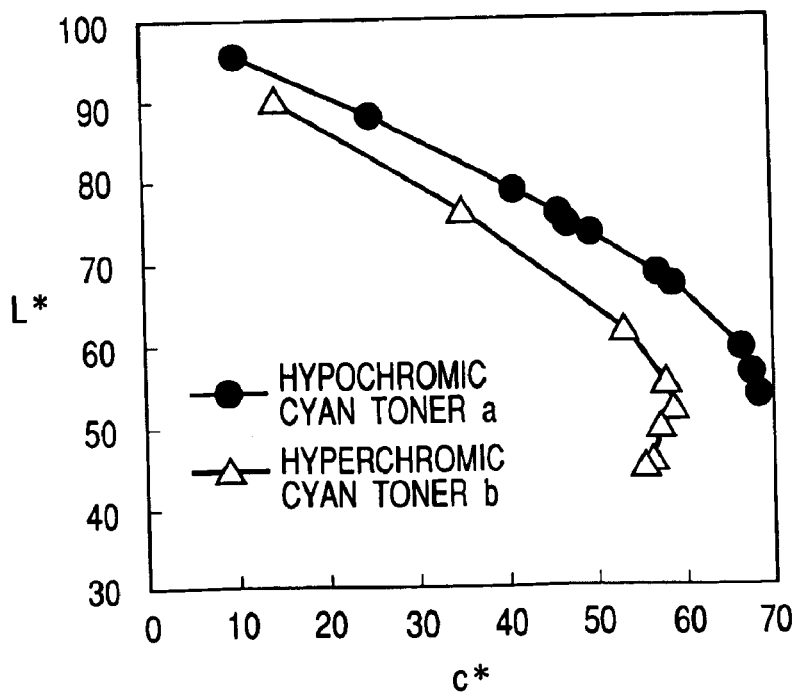
FIG. 4 is a chart showing an example of a chromaticity-luminocity curve of toners embodying the present invention.

For measuring a*, b*, c* and L* for example of a cyan toner, such cyan toner is charged in a commercially available plain paper color copying apparatus (color laser copying apparatus CLC1150; manufactured by Canon Inc.) while a plain paper (color laser copy paper TKCLA4; manufactured by Canon Inc.) is employed as an image receiver, and 200-line images of 16 gradation levels are formed by varying the toner amount on the paper. The obtained images are subjected to a measurement of a*, b* and L* with a densitometer SpectroScanTransmission (manufactured by Gretag Macbeth Inc.). The measurement is executed under conditions of an observing light source: D50, an observing field: 2°, a density: DINNB, a white standard: Paper and without filter. An a*-b* coordinate chart is prepared by plotting the obtained a* value in the abscissa and the obtained b* value in the ordinate, and a* values at b* of −20 and −30 are determined from the chart. Representative results of measurement are shown in FIG. 3. Then a value c* is obtained from the aforementioned equation (1), an L*-c* chart is prepared by plotting c* and L* respectively in the abscissa and in the ordinate, and an L* value at c* of 30 is determined from the chart. Representative results of measurement are shown in FIG. 4.

According to Japanese Patent Application Laid-Open No. 2002-144250, it is possible to avoid the aforementioned drawbacks and to provide a satisfactory image with excellent gradation without granularity from a low density area to a high density area, and with a wide color reproduction range by employing a hypochromic cyan toner a having an a* value (a−1) within a range from −19 to −30 at b*=−20 and an a* value (a−2) within a range from −29 to −45 at b*=−30, and a hyperchromic cyan toner b having an a* value (a−3) within a range from −7 to −18 at b*=−20 and an a* value (a−4) within a range from −10 to −28 at b*=−30.

The present embodiment provides a better result by giving an emphasis to the linearity of L*, but linearity on c* can also be secured in the present embodiment by employing toners of which difference in hue is suitably limited as described in Japanese Patent Application Laid-Open No. 2002-144250.

Figure 6:
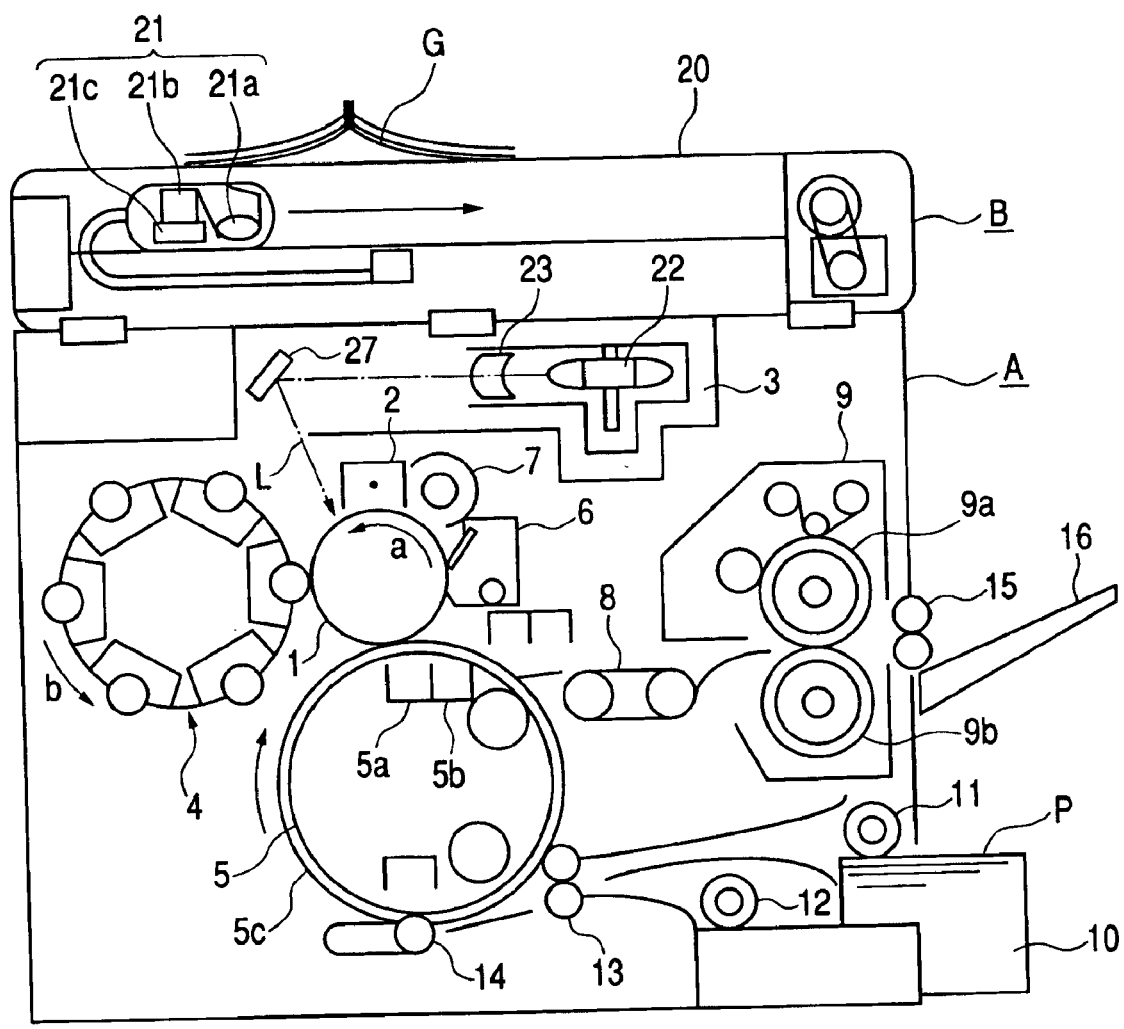
FIG. 6 is a longitudinal cross-sectional view showing the configuration of a laser beam copying apparatus (usable also as a printer) for forming a full-color image utilizing a hypochromic cyan toner, a hyperchromic cyan toner, a hypochromic magenta toner, a hyperchromic magenta toner, a yellow toner and a black toner suitable for the first embodiment.

For the purpose of an output test with 4 colors+2 colors according to the present invention, the aforementioned color laser copying apparatus CLC1150 (manufactured by Canon Inc.) was modified as shown in FIG. 6. In FIG. 6, there are shown a printer unit A, and an image reading unit (image scanner) B mounted on the printer unit A.

In the image reading unit B, an original G is placed, with a surface to be copied downward, on a glass plate of a copy board 20, and is pressed by an unrepresented original cover plate. An image reading unit 21 is provided with an original illuminating lamp 21a, a short-focus lens array 21b, a CCD sensor 21c etc.

In response to a depression of an unrepresented copy button, the image reading unit 21 is driven forward, under the glass plate 20 of the copy board, from a home position at a left-hand side thereof to a right-hand side, and is driven backward to the home position after reaching a predetermined end point of the forward motion.

In the course of the forward motion of the image reading unit 21, the downward image-bearing surface of the original G placed on the copy board glass plate 20 is illuminated in succession from the left-hand side toward the right-hand side by the original illuminating lamp 21a, and the light reflected from the original surface is focused by the short-focus lens array 21b onto the CCD sensor 21c.

The CCD sensor 21c is composed of a light receiving part, a signal transfer part and an output part (these parts not being shown), and an optical signal is converted in the light receiving part into a charge signal, which is transferred in the transfer part in succession in synchronization with clock pulses and converted in the output part into a voltage signal, which is outputted after amplification and a conversion into a low impedance. An analog signal thus obtained is converted by a known image processing into a digital signal for supply to the printer unit. In this manner, the image information of the original G is photoelectrically read by the image reading unit B as a time-sequential digital electrical pixel signal (image signal).

Figure 8:
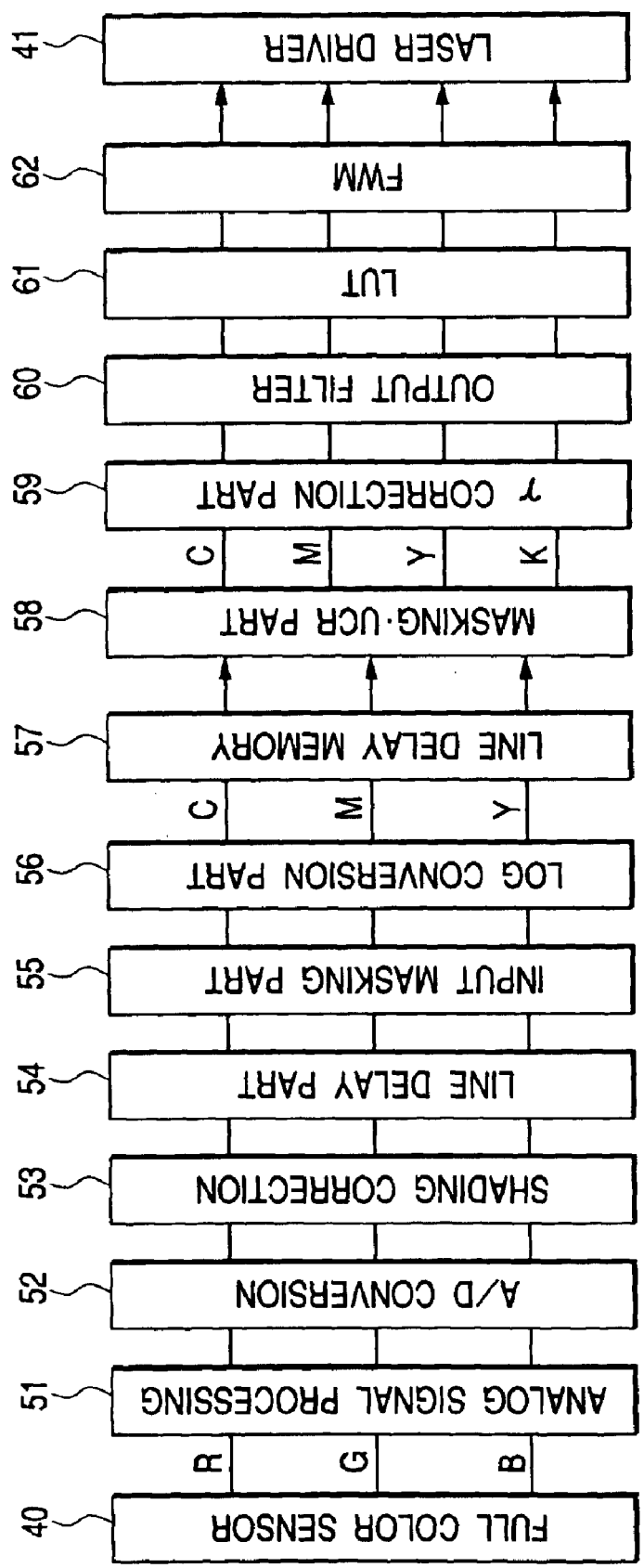
FIG. 8 is a block diagram showing an image processing.

FIG. 8 is a block diagram of image processing. Referring to FIG. 8, an image signal outputted from a full-color sensor 40, which is a CCD sensor, is supplied to an analog signal processing part 51 for gain and offset adjustment, then is subjected in an A/D conversion part 52 to a conversion, for each color component, into RGB digital signals of 8 bits (0 to 255; 256 gradation levels), and is further subjected, in a shading correction part 53, to a known shading correction in which a gain is optimized for each CCD sensor cell and for each color, utilizing a signal obtained by reading a standard white board (not shown) in order to eliminate a fluctuation in the sensitivity in each CCD sensor array.

A line delay part 54 compensates a spatial aberration contained in the image signals outputted from the shading correction part 53. Such spatial aberration results from a fact that the line sensors in the full-color sensor 40 are positioned with mutual predetermined distances in a sub scanning direction. More specifically, R (red) and G (green) color component signals are delayed in the unit of a line with respect to B (blue) color component signal thereby synchronizing three color component signals.

Figure 9:
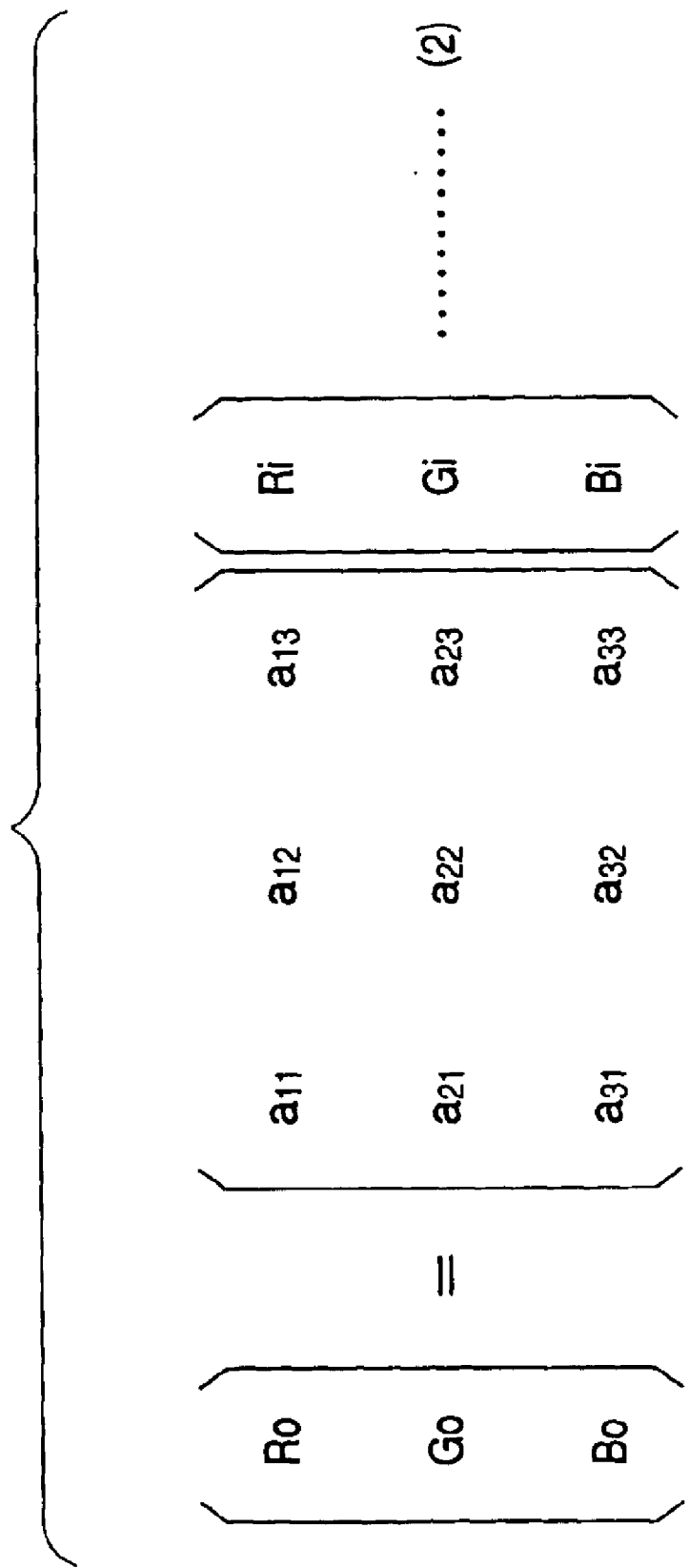
FIG. 9 is a view showing a matrix for converting a color space of image signals into a standard color space.

An input masking part 55 converts a color space of the image signal, outputted from the line delay part 54, into an NTSC standard color space by a matrix calculation represented by an equation (2) shown in FIG. 9. More specifically, each color component signal, outputted from the full-color sensor 40, belongs to a color space determined by the spectral characteristics of a color filter for each color component, and such color space is converted into the NTSC standard color space.

A LOG conversion part 56 is constituted of a look-up table (LUT) prepared for example in a ROM, and converts RGB luminance signals, outputted from the input masking part 55, into CMY density signals. A line delay memory 57 delays the image signals outputted from the LOG conversion part 56 by a period (line delay period) required by a black character discriminating part (not shown) for generating, from the output of the input masking part 55, control signals such as UCR, FILTER, SEN etc.

A masking-UCR part 58 extracts a black component signal K from the image signals outputted from the line delay memory 57, then applies a matrix calculation for compensating color turbidity in the color recording materials used in the printer unit on the YMCK signals, and outputs a color component image signals for example of 8 bits in the order of M, C, Y and K for each reading operation of the reader unit. The matrix coefficients to be used in the matrix calculation are set by a CPU (not shown).

Figure 12:
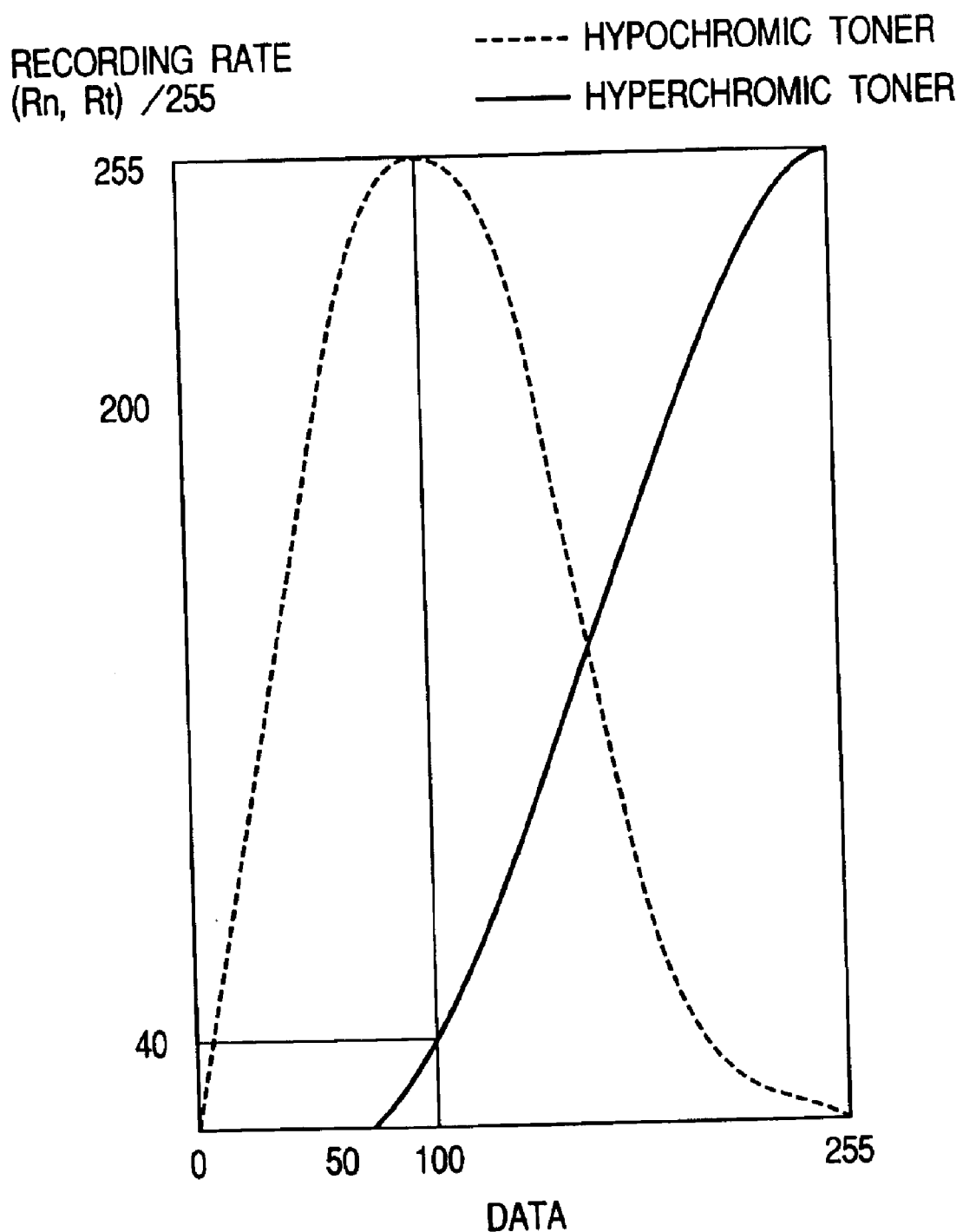
FIG. 12 is a chart showing a relationship between a recording rate with hypochromic toner and hyperchromic toner and gradation data in an embodiment of the present invention.

Then, based on thus obtained 8-bit color component image signal Data of cyan component and magenta component, there is executed a process of determining recording rates Rn, Rt of hyperchromic dot and hypochromic dot, by referring to FIG. 12. For example, in case an input gradation data Data is 100/255, the recording rate Rt of the hypochromic dot is determined as 255/255 and the recording rate Rn of the hyperchromic dot is determined as 40/255. The recording rate means a proportion of toner to be deposited in a predetermined area, and is represented by an absolute value taking 255 as 100%.

Thus, the amounts of the hyperchromic toner and the hypochromic toner are determined according to the input data, utilizing a chart in FIG. 12, providing the optimum amounts of the hyperchromic toner and the hypochromic toner according to the gradation. As shown in FIG. 12, image formation is executed solely with the hypochromic toner up to a predetermined level of the gradation signal Data. With an increase of the gradation signal Data beyond the predetermined level, the recording rate of the hyperchromic toner increases. At a gradation signal Data beyond a level 100, the recording rate of the hyperchromic toner increases but the recording rate of the hypochromic toner gradually decreases. At the maximum level 255 of the gradation signal Data, the recording rate of the hyperchromic toner becomes maximum and the recording rate of the hypochromic toner becomes zero.

The chart shown in FIG. 12 is prepared in such a manner, in case an input data Din is changed from a minimum value to a maximum value for varying the gradation level from a minimum level to a maximum level (entire gradation levels), that a lightness L* of a patch image satisfies a relation:

$$L^*(Din1) > L^*(Din2)$$

in case Din1<Din2 and that, over the entire gradation levels (particularly in a state where the hyperchromic toner starts to be mixed in the hypochromic toner), a change ΔL* in the lightness corresponding to 2% of the entire gradation levels is less than 10, preferably less than 5. The chart is at first prepared with initially known conditions such as the kinds of the toners, and is rewritten from time to time in the course of use, in response to a change in the conditions.

A γ correction part 59 executes a density correction on the image signals outputted from the masking-UCR part 58, in order to match the image signals with ideal gradation characteristics of the printer unit. An output filter (spatial filter processing part) 60 applies an edge enhancement or a smoothing process on the image signals outputted from the γ correction part 59, according to a control signal from a CPU.

An LUT 61, for matching the density of the output image with that of the original image, is constituted for example of a RAM, and a conversion table therein is set by the CPU. A pulse width modulator (PWM) 62 outputs a pulse signal of a pulse duration corresponding to the level of an input image signal, and such pulse signal is entered into a laser driver 41 for driving a semiconductor laser (laser light source).

The image forming apparatus is provided with a pattern generator (not shown) with a registered gradation pattern, whereby a signal can be directly transferred to the pulse width modulator 62.

An exposure apparatus 3 executes a laser scan exposure L, based on the image signal entered from the image reading unit 21, on the surface of the photosensitive member 1 which is a charged image bearing member, thereby forming an electrostatic latent image thereon.

Figure 10:
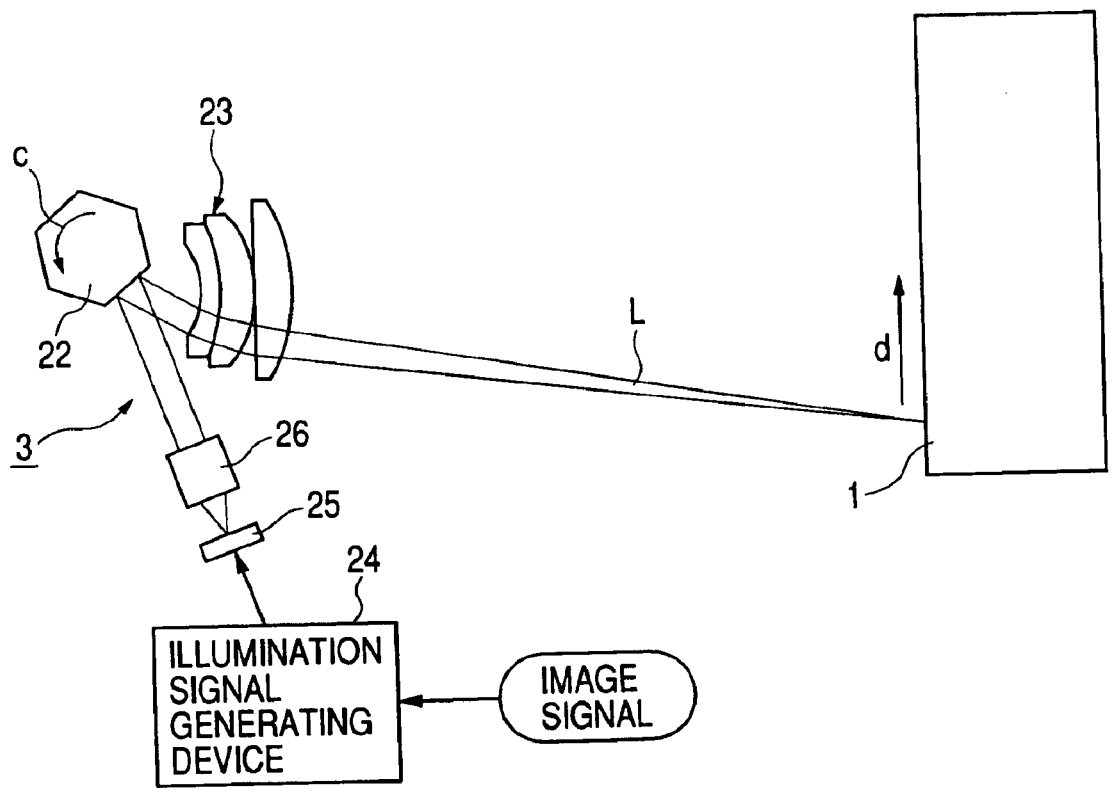
FIG. 10 is a view showing a laser exposure optical system in an embodiment of the present invention.
Figure 11:
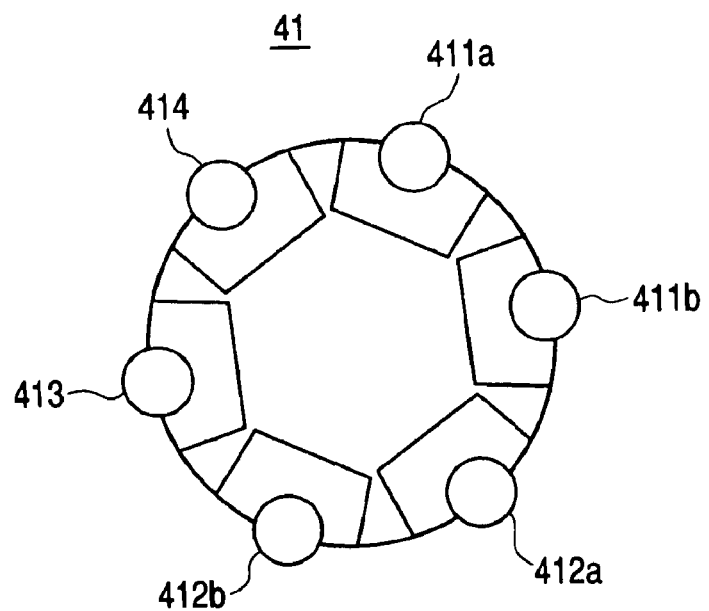
FIG. 11 is a schematic view showing the configuration of a developing apparatus in an embodiment of the present invention.

FIG. 10 is a schematic view showing the configuration of the exposure apparatus 3. For executing a laser scan exposure L on the photosensitive member 1 by the exposure apparatus 3, an illumination signal generating device 24 turns on and off a solid laser device 25 at predetermined timings based on the image signal entered from the image reading unit 21. A laser beam, constituting an optical signal emitted from the solid laser device 25, is converted by a collimating lens system 26 into a substantially parallel light beam, which is put into a scanning motion in a direction d (longitudinal direction) on the photosensitive member 1 by a rotary polygon mirror 22, rotated at a high speed in a direction c, whereby a laser spot is focused on the surface of the photosensitive member 1 through an fθ lens group 23 and a mirror (cf. FIG. 1). Such laser scan forms an exposure distribution of a scan line on the surface of the photosensitive member 1, and is made to displace by a predetermined amount in a perpendicular direction for each scanning motion with respect to the surface of the photosensitive member 1, thereby forming an exposure distribution corresponding to the image signal thereon.

Thus, by scanning the uniformly charged surface (charged at −700 V in the present embodiment) of the photosensitive member 1 with the light of the solid laser device 25 which is turned on and off according to the image signal through the rotary polygon mirror 22, electrostatic latent images of respective colors are formed in succession on the surface of the photosensitive member 1, corresponding to the scan exposure patterns.

A developing apparatus 4 includes, respectively in developing devices 411a, 411b, 412a, 412b, 413, 414 and 415, a developer containing a cyan toner a, a developer containing a cyan toner b, a developer containing a magenta toner a, a developer containing a magenta toner b, a developer containing a yellow toner and a developer containing a black toner, and serves to develop the electrostatic latent images formed on the photosensitive member 1, constituting a latent image bearing member, by a magnetic brush developing method thereby forming toner images of respective colors on the photosensitive member 1. A preferred example of such developing devices is a two-component developing device shown in FIG. 7. For example the developing devices 411a and 411b respectively constitute a first toner containing portion and a second toner containing portion.

Figure 7:
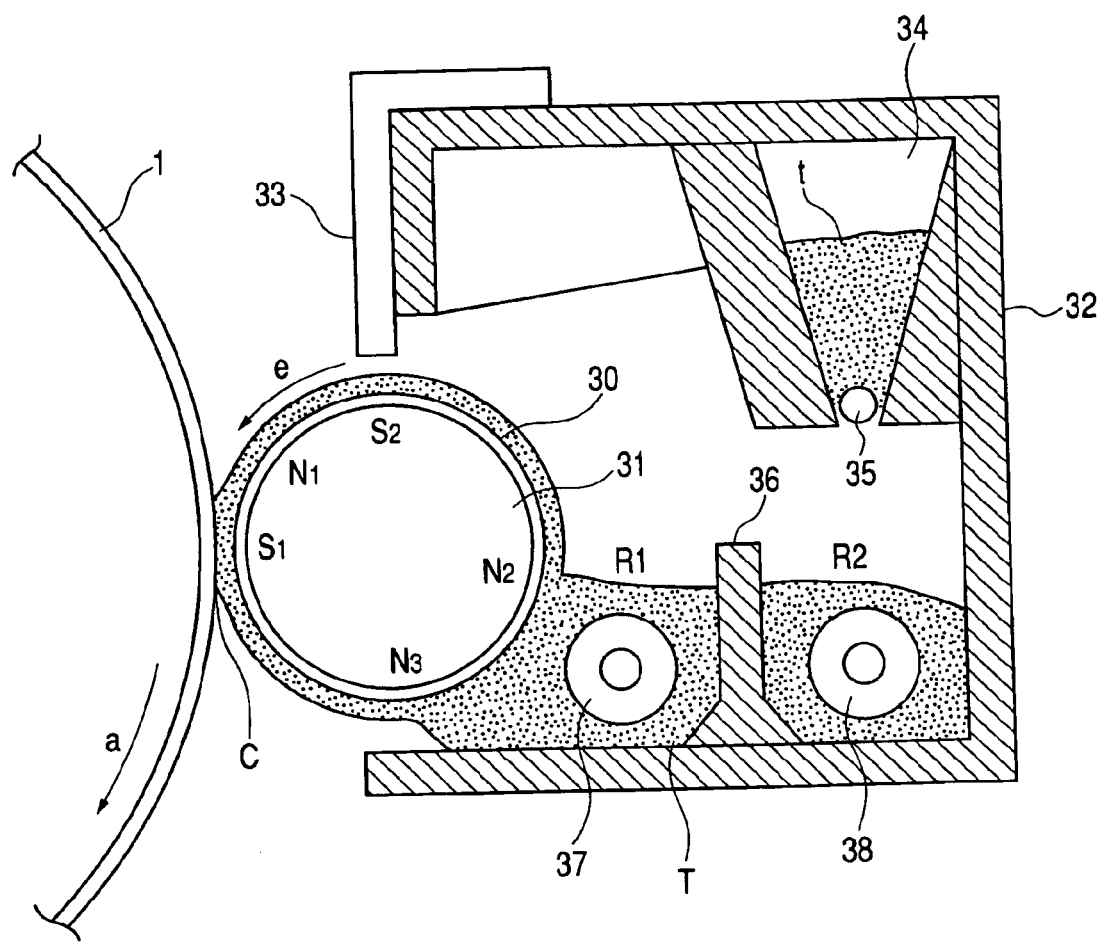
FIG. 7 is a longitudinal cross-sectional view showing the configuration of a two-component developing device.

Referring to FIG. 7, the two-component developing device is provided with a developing sleeve 30, which is a developer carrying member rotated in a direction e, and also with a fixed magnet roller 31 inside the developing sleeve 30. A developing container 32 is provided with a regulating blade 33 for forming a thin layer of a developer T on the surface of the developing sleeve 30.

The interior of the developing container 32 is separated by a partition 36 into a developing chamber (first chamber) R1 and an agitating chamber (second chamber) R2, and a toper hopper 34 is provided above the agitating chamber R2. In the developing chamber R1 and the agitating chamber R2, there are respectively provided carrying screws 37, 38. The toner hopper 34 is provided with a supply aperture 35, through which toner t is dropped to the agitating chamber R2 at the toner replenishment.

Also, the developing chamber R1 and the agitating chamber R2 respectively contain a developer T, constituted by a mixture of particles of the aforementioned toner and particles of a magnetic carrier.

The developer T in the developing chamber R1 is carried along the longitudinal direction of the developing sleeve 30 by the rotation of the carrying screw 37. The developer T in the agitating chamber R2 is carried along the longitudinal direction of the developing sleeve 30 by the rotation of the carrying screw 38. A developer carrying direction of the screw 38 is opposite to that of the screw 37.

The partition 36 is provided with apertures (not shown) at front and back in a direction perpendicular to the plane of the drawing, and the developer T carried by the carrying screw 37 is transferred to the carrying screw 38 through one of the apertures, while the developer T carried by the carrying screw 38 is transferred to the carrying screw 37 through the other of the apertures. The toner is charged, by a friction with the magnetic carrier particles, in a polarity for developing the electrostatic latent image.

The developing sleeve 30, formed by a non-magnetic material such as aluminum or non-magnetic stainless copper, is positioned in an aperture of the developer container 32 close to the photosensitive member 1, and is rotated in a direction e (counterclockwise) thereby carrying the developer T, constituted by a mixture of the toner and the carrier, to a developing portion C. A magnetic brush formed by the developer T carried on the developing sleeve 30 comes into contact, in the developing portion C, with the photosensitive member 1 rotated in a direction a (clockwise), thereby developing the electrostatic latent image in such developing portion C.

The developing sleeve 30 is given, by a power supply (not shown), an oscillating bias voltage, formed by superposing a DC voltage on an AC voltage. A dark portion potential (potential of non-exposed area) and a light portion potential (potential of exposed area) of the electrostatic latent image are positioned between a maximum value and a minimum value of the above-mentioned oscillating bias voltage. Thus, at the developing portion C, there is generated an alternating electric field of which direction alternates. In such alternating electric field, the toner and the carrier cause vigorous vibrations, whereby the toner is liberated from the electrostatic attractive force of the developing sleeve 30 and the carrier and is deposited in a light area of the electrostatic latent image on the surface of the photosensitive member 1.

The oscillating bias voltage has a difference between the maximum and minimum values (peak-to-peak voltage) preferably within a range from 1 to 5 kV, and was selected in the present embodiment as a rectangular wave of 2 kV, and also has a frequency within a range of 1 to 10 kHz, which was selected as 1 kHz in the present embodiment. The form of the oscillating bias voltage is not limited to a rectangular wave but can also be a sinusoidal wave, a triangular wave etc.

The DC voltage component mentioned above is positioned between the dark potential and the light potential of the electrostatic latent image, but is preferably closer in the absolute value to the dark potential than to the minimum light potential, in order to prevent fogging deposition of the toner in the dark potential area. In the present embodiment, for a dark potential of −700 V, there were selected a light potential of −200 V and a DC component of −500 V in the developing bias voltage. Also a minimum gap (positioned in the developing portion C) between the developing sleeve 30 and the photosensitive member 1 is preferably within a range of 0.2 to 1 mm, and was selected as 0.5 mm in the present embodiment.

Also an amount of the developer T, regulated by the regulating blade 33 and carried to the developing portion C, is preferably such that the magnetic brush of the developer T, formed by a magnetic field in the developing portion C formed by a developing magnetic pole S1 of the magnet roller 31, has a height on the surface of the developing sleeve 30 corresponding to 1.2 to 3 times of the minimum gap between the developing sleeve 30 and the photosensitive member 1 in a state where the photosensitive member 1 is eliminated. In the present embodiment, the height was selected as 700 $\mu$m.

The developing magnetic pole S1 of the magnet roller 31 is provided in a position opposed to the developing portion C, and a magnetic brush of the developer T is formed by a developing magnetic field generated by such developing magnetic pole S1 in the developing portion C and comes into contact with the photosensitive member 1 thereby causing a development of the electrostatic latent image constituted of a distribution of dots. In such developing operation, not only the toner present in such brush of the magnetic carrier but also the toner present on the surface of the developing sleeve are transferred to an exposed area of the electrostatic latent image thereby achieving the development.

The developing magnetic field generated by the developing magnetic pole S1 preferably has a peak intensity on the surface of the developing sleeve 30 (magnetic flux density in a direction perpendicular to the surface of the developing sleeve 30) within a range from $5 \times 10^{-2}$ to $2 \times 10^{-1}$ (T). The magnetic roller 31 is provided, in addition to the developing magnetic pole S1, with poles N1, N2, N3 and S2.

In the following, there will be explained a development step for rendering visible an electrostatic latent image on the surface of the photosensitive member 1 by a two-component magnetic brush development method by the developing apparatus 4, and a circulating system for the developer T.

The developer T, picked up by a pole N2 in the course of rotation of the developing sleeve 30, is carried through poles S2 and N1 and is subjected to a thickness regulation by the regulating blade 33 thereby forming a thin layer of the developer. Then the developer T formed as a brush by the magnetic field of the developing magnetic pole S1 develops the electrostatic latent image on the photosensitive member 1. Thereafter, the developer T on the developing sleeve 30 drops into the developing chamber R1 by a repulsive magnetic field between magnetic poles N3 and N2. The developer T dropping into the developing chamber R1 is agitated and carried by the carrying screw 37.

In the present embodiment, an intermediate transfer member and transfer means may be constituted by ordinary materials.

A transfer member 5 is provided, on a surface thereof, with a transfer sheet 5c formed for example by a polyethylene terephthalate film and is so positioned as to be contacted with or separated from the photosensitive member 1. The transfer member 5 is rotated in a direction indicated by an arrow (clockwise direction). Inside the transfer member 5, there are provided a transfer charger 5a, a separating charger 5b. etc.

In the following there will be given an explanation on an image forming operation of the above-described image forming apparatus.

The photosensitive member 1 is rotated in a direction a (counterclockwise) with a predetermined peripheral speed (process speed) about a central axis, and is subjected, in the course of such rotation, to a uniform charging, which is of negative polarity in the present embodiment.

The uniformly charged surface of the photosensitive member 1 is subjected to the scan exposure L by the laser light, which is emitted from the exposure apparatus (laser scanning apparatus) 3 and modulated according to the image signal supplied from the image reading unit B to the printer unit A, whereby electrostatic latent images are formed in succession on the photosensitive member 1, corresponding to the respective colors of the image information of the original G photoelectrically read by the image reading unit B. The electrostatic latent image formed on the photosensitive member 1 is subjected to a reversal development by the aforementioned magnetic brush development method in the developing apparatus 4, thereby providing a visible toner image of a first color at first by the developing device 411a.

On the other hand, in synchronization with the formation of the aforementioned toner image on the photosensitive member 1, a transfer material (transfer receiving member) P such as paper, contained in a paper cassette 10, is fed one by one by a feed roller 11 or 12 and conveyed by registration rollers 13 at a predetermined timing to the transfer member 5, and is electrostatically attracted to the transfer member 5, serving as a transfer material carrying member, by means of an attraction roller 14. The transfer material P, electrostatically attracted on the transfer member 5, then is moved to a position opposed to the photosensitive member 1 by a rotation of the transfer member 5 in a direction indicated by an arrow (clockwise direction), and a transfer charger 5a gives a charge of a polarity opposite to that of the toner on a rear surface of the transfer material P whereby a front surface thereof receives a transfer of the toner image from the photosensitive member 1.

After such transfer, residual toner remaining on the photosensitive member 1 is removed by a cleaning apparatus 6 and is used for forming subsequent toner images.

Thereafter the electrostatic latent images on the photosensitive member 1 are similarly developed, whereby a cyan toner image a, a cyan toner image b, a magenta toner image a, a magenta toner image b, a yellow toner image and a black toner image formed on the photosensitive member 1 are transferred by the transfer charger 5a in superposition on the transfer material P borne on the transfer member 5, thereby forming a full-color image.

Then the transfer material P is separated from the transfer member 5 by a separating charger 5b, and is conveyed through a conveyor belt 8 to a fixing apparatus 9. The transfer material P enters the fixing apparatus 9 with a speed of about 200 mm/sec, and is subjected to a heating at about 160° C. and a pressing at 70 kg between a fixing roller 9a (silicone rubber of a thickness of 2.4 mm, a diameter of 60 mm and a hardness 79 (ASKER-C hardness under a load of 1 kg)) and a pressure roller 9b (silicone rubber of a thickness of 1.8 mm, a diameter of 60 mm and a hardness 81 (ASKER-C hardness under a load of 1 kg)) to fix the full-color image on the surface, and is discharged onto a tray 16 by discharge rollers 15.

The surface of the photosensitive member 1 is subjected to a cleaning of the residual toner by the cleaning apparatus 6 and to a charge elimination by a pre-exposure lamp 7, thereby being prepared for a next image formation.

Figure 5A:
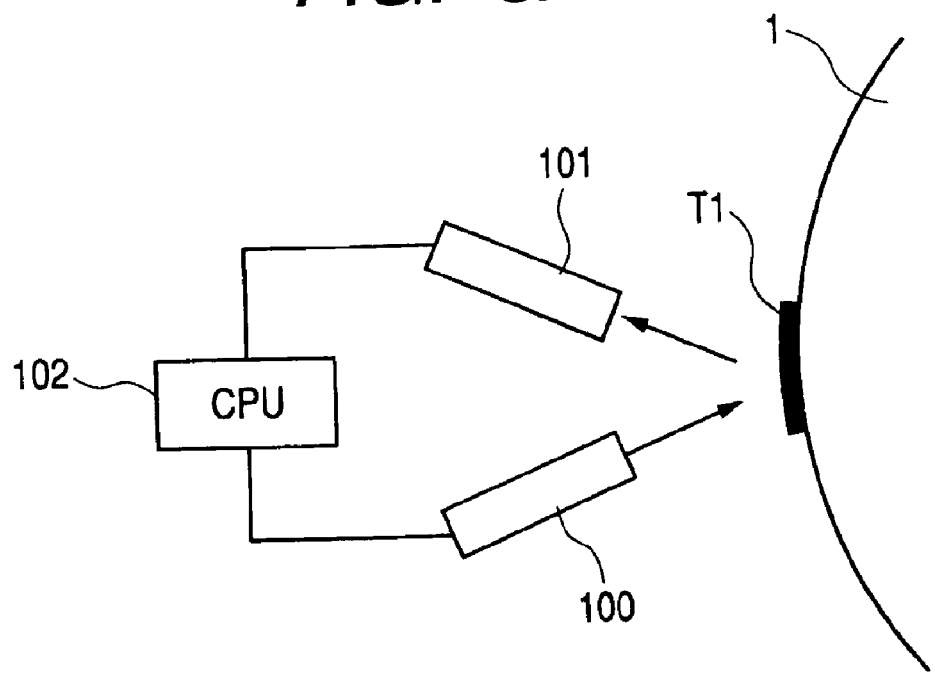
FIG. 5A is a view showing the configuration of an optical sensor for reaching a patch image on a photosensitive member in a first embodiment.
Figure 5B:
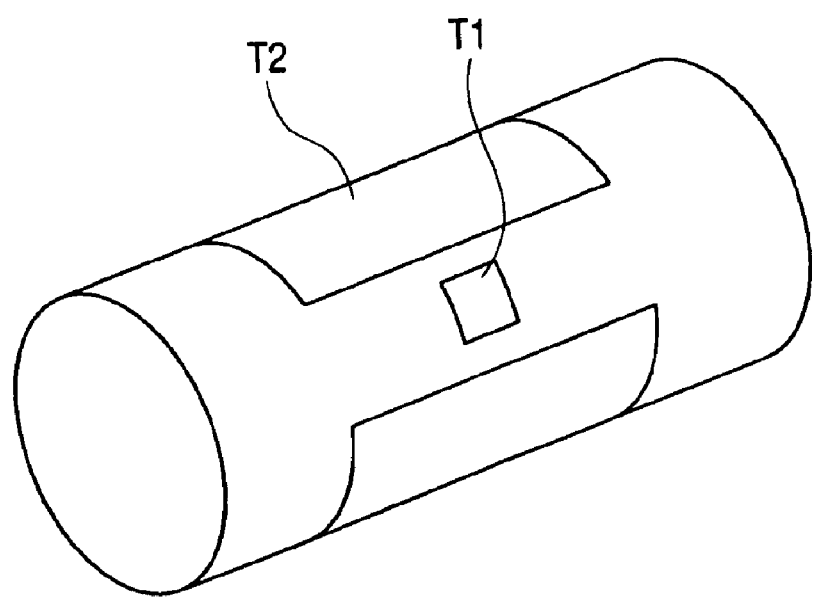
FIG. 5B is a view showing a state of a patch image formed in a non-image area of the photosensitive member.

In the present embodiment, in order to check an image quality (in order to detect the image density) prior to an actual image output, there is formed a patch image between the transfer material on the transfer member 5, as represented by T1 in FIG. 5B (T2 in FIG. 5B being an actual image).

At first, for the aforementioned hypochromic cyan toner, a latent image of a recording rate of 50% (corresponding to 128/255 on the ordinate in FIG. 12) is recorded with the laser beam and is subjected to a development process with a development bias voltage containing an ordinarily employed DC component thereby forming a toner image T1 on the photosensitive drum 1.

An illuminating light, emitted from a light emitting part 100 shown in FIG. 5A, is reflected by the patch image T1 formed on the photosensitive drum 1, and the reflected light is received by a light receiving part 101. An amount of such reflected light is converted by a CPU 102 into an output voltage. In case the obtained value L* is not a desired value, the DC component of the developing bias (developing condition) applied to the aforementioned developing sleeve is changed by an estimated amount in order to prepare for the actual image output. Such estimated amount is, for example, a difference between the value obtained by the patch image measurement and the desired value. The light emitting part 100, the light receiving part 101 and the CPU 102 shown in FIG. 5A constitute image quality checking means (density detecting means).

In case there is a margin in time, it is desirable to form a patch image again on the photosensitive member and to confirm that the varied bias value is acceptable.

Also in case a toner content in the developer is judged low, it is desirable to replenish new toner from the toner hopper 34 into the developing container, thereby bringing the remaining toner amount to a predetermined amount.

The judgment whether the toner content in the developer is low can be achieved by memorizing a relationship between the developing bias and the luminocity at an optimum toner content at an initial state and comparing the measured value with such memorized relationship.

Then an image quality check is conducted similarly by a patch image, for the hyperchromic cyan toner. Based on such image quality check, the developing bias voltage (developing condition) applied to the developing sleeve is controlled. Thus, for cyan toners of a substantially same hue, the density of the hypochromic toner image and that of the hyperchromic toner image are separately detected by the density detecting means and the developing condition for the hypochromic toner and that for the hyperchromic toner are controlled according to the results of such detection.

The above-described steps are similarly executed on the hypochromic and hyperchromic magenta toners. More specifically, for magenta toners of a substantially same hue, the density of the hypochromic toner image and that of the hyperchromic toner image are separately detected by the density detecting means.

In this manner it is rendered possible, even in an unstable electrophotographic process, to obtain pale and dense images without granularity over the entire gradation range. It is also possible to control, instead of the developing condition, another output image forming condition on the transfer material such as a latent image forming condition, a transfer condition or a fixing condition.

(Second Embodiment)

Figure 13:
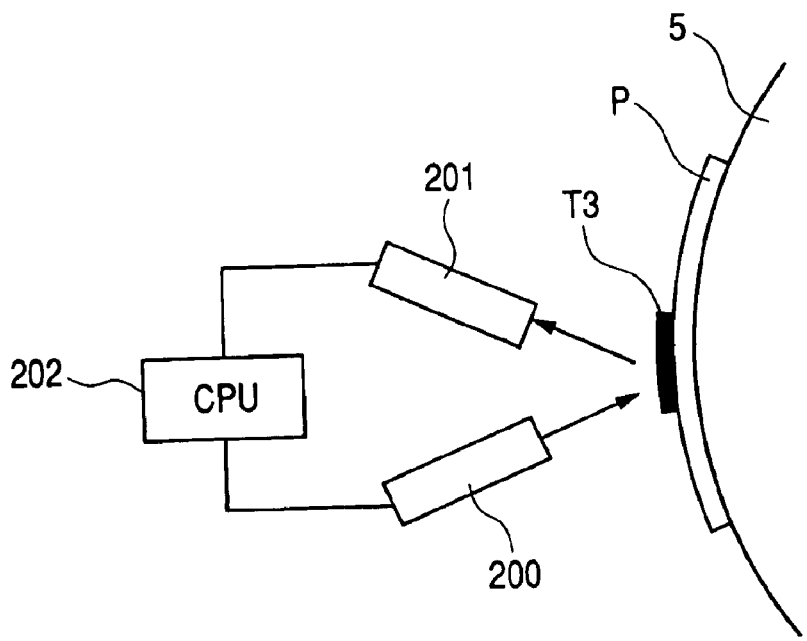
FIG. 13 is a view showing the configuration of an optical sensor for reaching a patch image on a photosensitive member in a second embodiment.

In the present embodiment, there is formed, on the transfer material P carried on the transfer member 5 as shown in FIG. 13 prior to the actual image output, a patch image constituted of an almost solid hypochromic toner image and a hyperchromic toner image of a small amount as in a highlight output, for example a superposed toner image with a hypochromic toner recording rate of 100% (255/255) and a hyperchromic toner recording rate of about 16% (40/255), corresponding to a state Data=100 in FIG. 12.

Other configurations and functions are similar to those in the first embodiment. Therefore, same components will be represented by same numbers and will not be explained further.

At first, for the aforementioned hypochromic cyan toner, a latent image of a recording rate of 100% (corresponding to 255/255 on the ordinate in FIG. 12) is recorded and is subjected to a development process with a development bias voltage containing an ordinarily employed DC component thereby forming a toner image on the photosensitive drum 1, and such toner image is transferred onto the transfer material P as explained in the foregoing.

Figure 14:
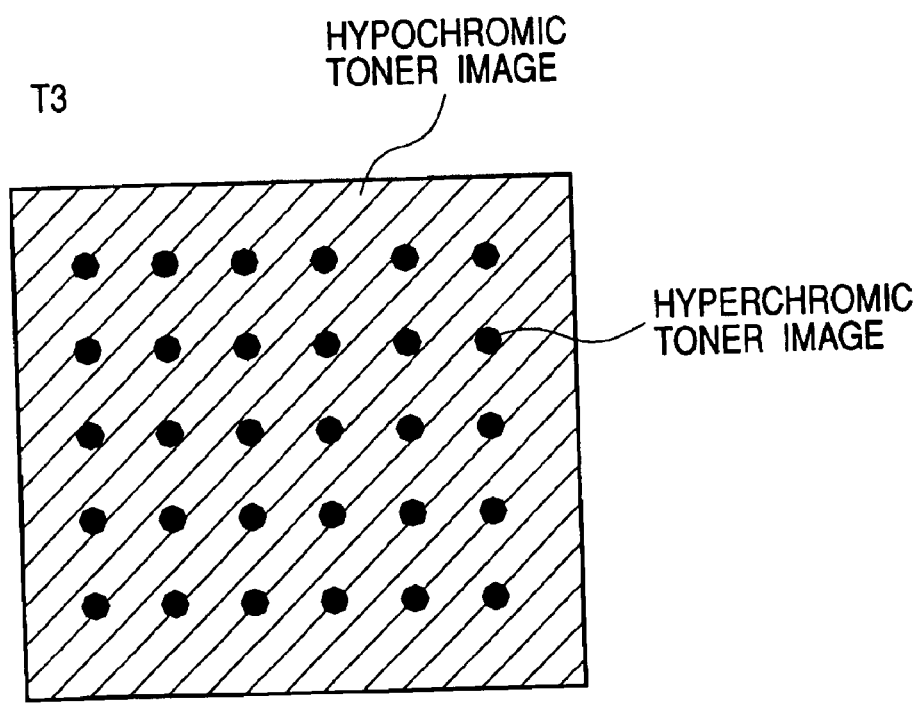
FIG. 14 is a plan view of an image patch containing hyperchromic toner and hypochromic toner in mixed manner in a second embodiment.

Then, for the hyperchromic toner, a latent image of a recording rate of 16% is recorded, then developed and is transferred in superposition onto the already formed hypochromic toner patch image, thereby obtaining a hyperchromic-hypochromic mixed toner image (patch image) T3. FIG. 14 shows such patch image T3 seen from above. In such patch image, as shown in FIG. 14, the hyperchromic toner has a recording rate smaller than that of the hypochromic toner.

An illuminating light, emitted from a light emitting part 200 shown in FIG. 13, is reflected by the patch image T3 formed on the transfer material P, and the reflected light is received by a light receiving part 201. An amount of such reflected light is converted by a CPU 202 into an output voltage. In case the obtained value L* is not a desired value, the DC components of the developing biases applied to the developing sleeves for the hyperchromic toner and the hypochromic toner are changed by estimated amounts in order to prepare for the actual image output. The light emitting part 200, the light receiving part 201 and the CPU 202 shown in FIG. 13 constitute an optical sensor constituting image quality checking means (density detecting means).

In case there is a margin in time, it is desirable to form a patch image again on the transfer material and to confirm that the varied bias values are acceptable.

Also in case a toner content in the developer is judged low, it is desirable to replenish new toner from the toner hopper 34 into the developing container, thereby bringing the remaining toner amount to a predetermined amount.

Then the above-described steps are similarly executed on the hypochromic and hyperchromic magenta toners.

In this manner it is rendered possible, even in an unstable electrophotographic process, to obtain pale and dense images without granularity over the entire gradation range.

In the present embodiment, the patch image is formed on the transfer material P borne on the transfer member 5, but, in case of an application to a system utilizing an intermediate transfer member, a similar effect can be obtained by forming a hyperchromic-hypochromic mixed toner patch image on such intermediate transfer member.

Also in case of a multiple development system, a similar effect can be obtained by forming a hyperchromic-hypochromic mixed toner patch image on the photosensitive member and executing an image quality check as in the first embodiment.

(Third Embodiment)

In case of an image quality check with a patch image containing the hyperchromic toner and the hypochromic toner in mixture as in the second embodiment, there may result a situation where it is not possible to judge whether to change the amount of the hyperchromic toner or to change the amount of the hypochromic toner.

In the present embodiment, therefore, the image quality check is executed at first with a patch image of the hypochromic toner only formed on the transfer material P carried on the transfer member, and then with a patch image containing the hypochromic toner and the hyperchromic toner in mixture, formed by transferring the hyperchromic toner in superposition. Otherwise, the patch image of the hypochromic toner is made larger while the patch image of the hyperchromic toner to be transferred in superposition is made smaller, thus forming a hyperchromic-hypochromic mixed toner patch image only in a part of the hypochromic patch image, and the image quality check is executed on both of the patch image of the hypochromic toner only and the patch image containing the hypochromic toner and the hyperchromic toner as a mixture.

It is also possible to estimate the transfer efficiency for each of the hyperchromic toner and the hypochromic toner thereby appropriately adjusting the transfer biases, by at first executing the image quality check with patch images formed respectively with the hyperchromic toner and the hypochromic toner on the photosensitive member as in the first embodiment and then executing the image quality check on the patch image formed on the transfer material P carried on the transfer member as in the present embodiment. Since a control on the transfer bias in the transfer process can suppress deterioration of the granularity at the transfer process, such method can provide a multiplying effect in reducing the granularity.

Also, since the true density, luminocity, hue and luster appear after passing the fixing device 9, it is desirable to collect data from a hyperchromic-hypochromic mixed toner patch image present on the transfer material after image fixation in order to achieve a more accurate feedback.

It is furthermore possible to improve the granularity, based on such data, to alter the conditions not only of the developing apparatus 4 and the transfer apparatus 5 but also of the fixing apparatus.

It is also possible, instead of controlling the developing condition (developing bias voltage), to control a latent image forming condition such as a light amount of the laser scanner.

In case means for adjusting (controlling) the quality of the image transferred to the transfer material based on the result of comparison of the patch image is present in all the latent image forming process, the developing process, the transfer process and the fixing process, it is possible to identify a process to be optimized for obtaining a desired luminocity, for example by executing an optimization from the upstream side of the entire process, namely from the latent image forming process, then, if the image quality is still not improved, by optimizing the developing process for example by varying the developing bias utilizing a patch image formed on the photosensitive member and prior to the transfer, and then by executing the optimization on the transfer process and the fixing process. Stated differently, for controlling the image forming conditions based on the result of detection of the patch image, there may be controlled at least one of the latent image forming condition, the developing condition, the transfer condition and the fixing condition.

Finally, there will be explained a result of measurement when the present embodiment was applied.

Two toners of different density levels were prepared by changing a content of a same colorant to obtain a hypochromic magenta toner and a hyperchromic magenta toner in the following manner.

<Hyperchromic Magenta Toner>

Polyester resin (100 parts by weight)/C.I. Pigment Red (5 parts by weight);

<Hypochromic Magenta Toner>

Polyester resin (100 parts by weight)/C.I. Pigment Red (1 parts by weight).

The above-mentioned materials were preliminarily mixed by a Henschel mixer, then melt kneaded by a two-axis extrusion kneader and, after cooling, crude crushed with a hammer mill into a size of 1 to 2 mm.

Then the product was fine crushed by an air-jet fine crusher, and the obtained fine crushed product was classified to obtain a hyperchromic magenta toner and a hypochromic magenta toner of a weight-averaged particle size of 5.6 $\mu$m.

Figure 15:
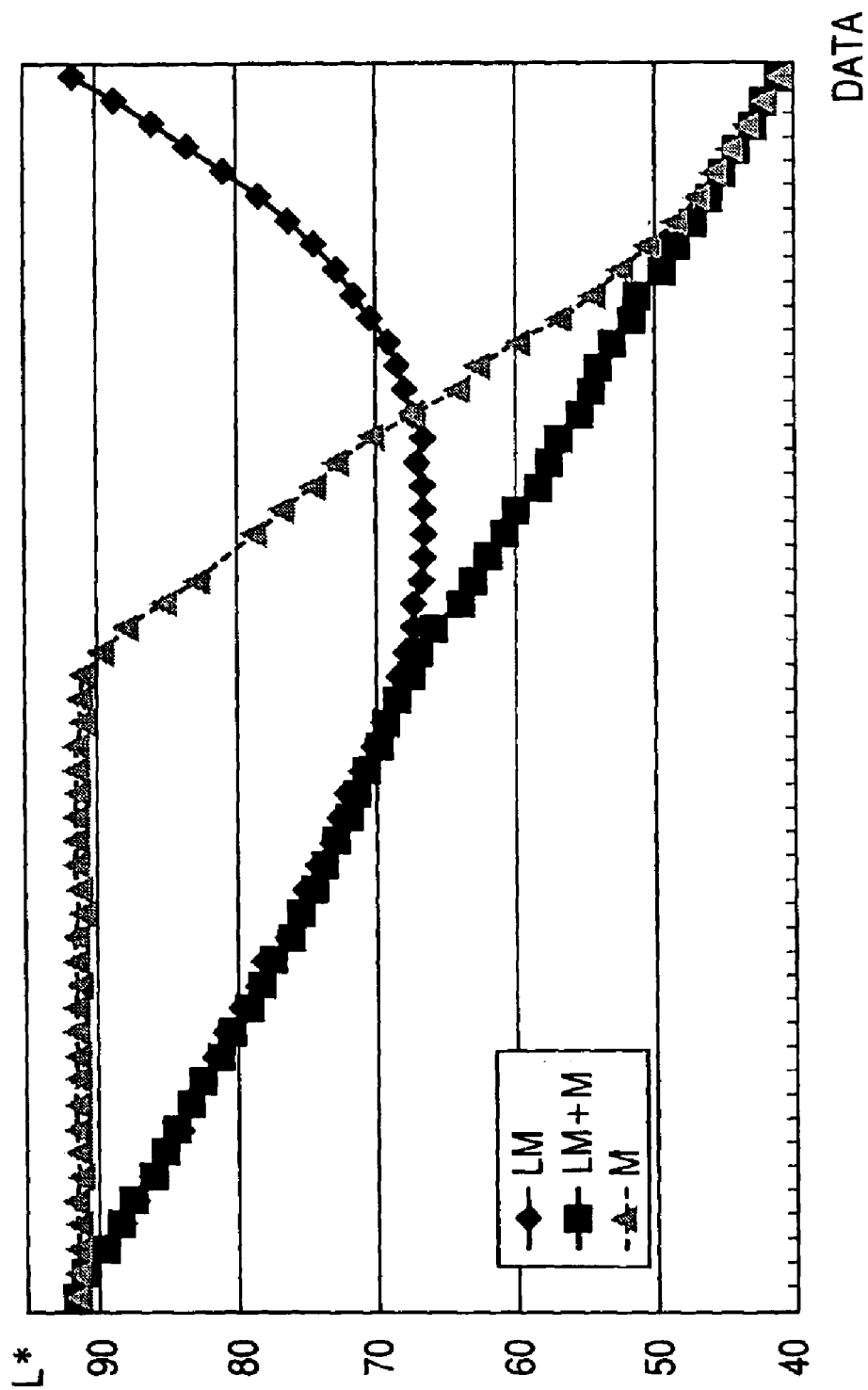
FIG. 15 is a chart showing gradation characteristics L* as a function of data (Din) for a hyperchromic toner patch image (M), a hypochromic toner patch image (LM) and a hyperchromic-hypochromic mixed toner patch image (LM+M) of magenta color in case an embodiment of the present invention is applied.

The obtained toners were used in the aforementioned apparatus for preparing a Data-recording rate table as shown in FIG. 12 (table in FIG. 12 being merely for explanation and different from the actually used data), and optimizations of the Data-recording rate table, the toner concentration in the developer, the developing bias, the transfer bias and the fixing condition were made by feedback controls based on the image quality check of the patch image after image fixation. FIG. 15 shows the gradation characteristics L* as a function of Data (Din), for each of a hyperchromic magenta toner patch image (M), a hypochromic magenta toner patch image (LM) and a hyperchromic-hypochromic mixed toner patch image (LM+M).

As shown in FIG. 15, the lightness changes almost linearly over the entire gradation range, and the granularity is maintained in a satisfactory level even in a medium density range where the hyperchromic toner and the hypochromic toner are present mixedly.

Figure 16:
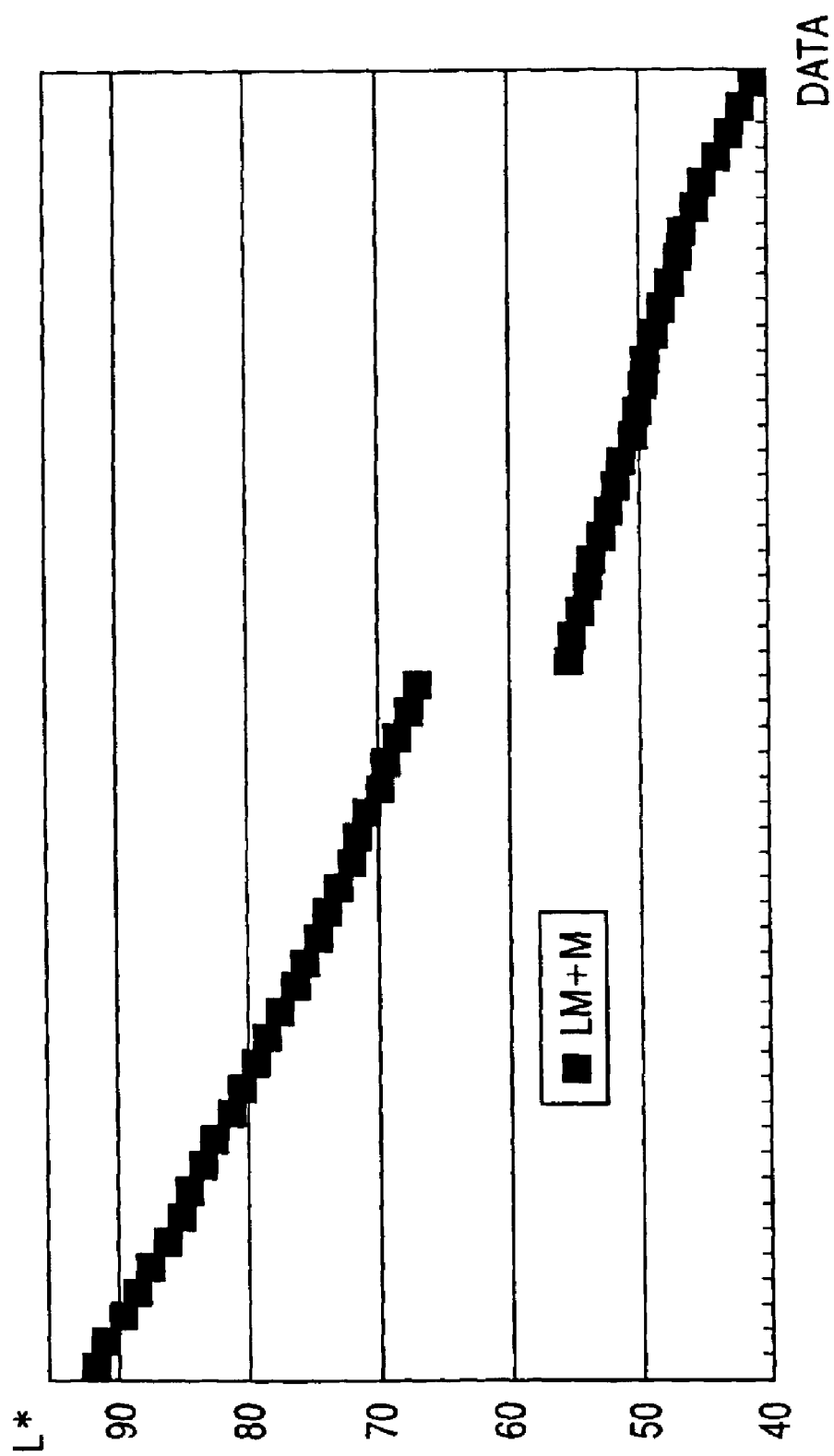
FIG. 16 is a chart showing gradation characteristics L* as a function of data (Din) for a hyperchromic-hypochromic mixed toner patch image (LM+M) in case an embodiment of the present invention is not applied.
Figure 17:
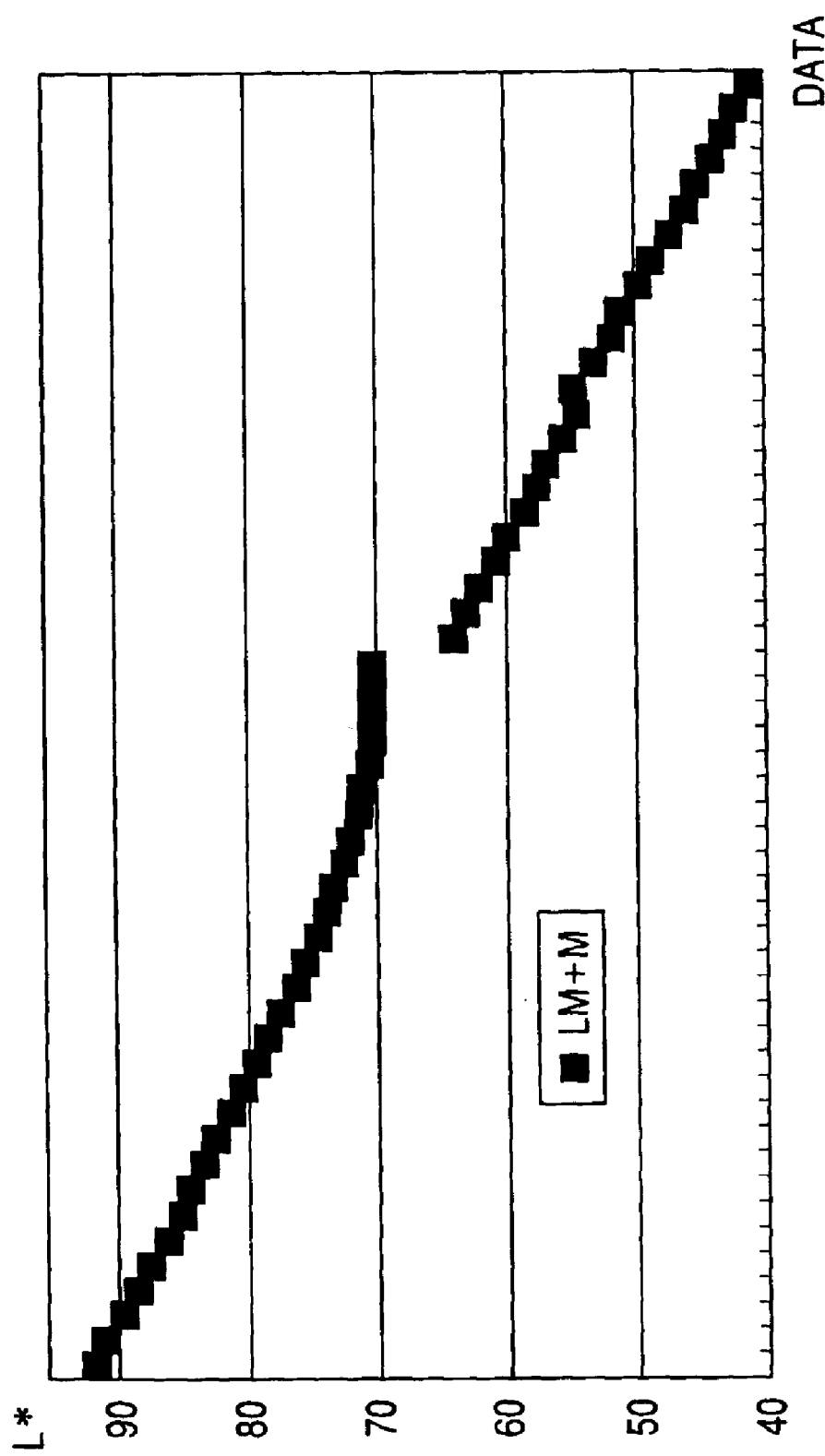
FIG. 17 is a chart showing gradation characteristics L* as a function of data (Din) for a hyperchromic-hypochromic mixed toner patch image (LM+M) in case an embodiment of the present invention is not applied.
Figure 18:
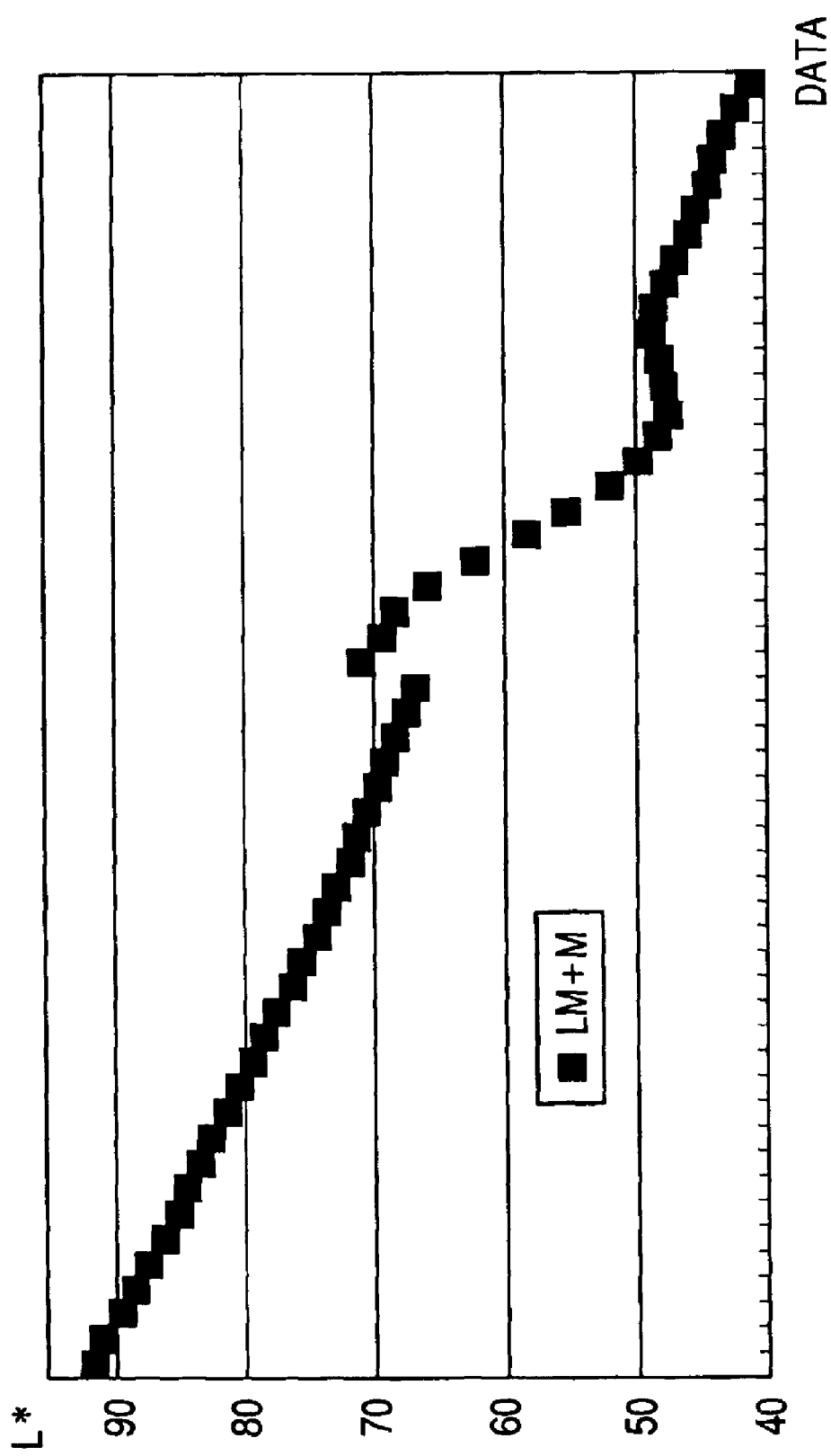
FIG. 18 is a chart showing gradation characteristics L* as a function of data (Din) for a hyperchromic-hypochromic mixed toner patch image (LM+M) in case an embodiment of the present invention is applied.

On the other hand, FIGS. 16, 17 and 18 show troubles encountered in case the adjustment of the image quality explained in the foregoing embodiments is not adopted.

In a case shown in FIG. 16, the developing bias of the developing device for the hyperchromic toner was not optimized, so that the development with the hyperchromic toner was executed with an excessively large amount to result in so-called "tone jump" at an intermediate range where the hyperchromic toner starts to be mixed. Besides, such difference in the luminocity, as large as about 13, significantly deteriorated the image quality particularly in outputting a natural image.

In a case shown in FIG. 17, the developing bias of the developing device for the hypochromic toner was not optimized, so that the development with the hypochromic toner was executed with an excessively large amount to result in so-called "tone jump" at an intermediate range where the hyperchromic toner starts to be mixed. Such difference in the lightness was about 6. Since it was confirmed that, in case of employing the hyperchromic toner and the hypochromic toner and in case the hypochromic toner is present in an almost solid state while the hyperchromic toner is present in a small amount, the difference in lightness is alleviated at a level less than 10 and is practically acceptable at a level less than 5, the image quality is better than the case shown in FIG. 16, but is preferably maintained at a lightness difference less than 5.

In a case shown in FIG. 18, the Data-recording rate table was not optimized in a state where the toner concentration in the developing device for the hyperchromic toner was lower than an appropriate level, so that, at the junction to the hyperchromic toner, the lightness does not show a monotonous decrease (with a decrease in the density) with an increase in the Data. Then the use of the Data-recording rate table in a state without matching of the concentration of the toners resulted in a peak and a valley in the lightness, thereby generating a signifant pseudo contours on the output natural image. Presence of such peak and valley in the lightness is a most undesirable phenomenon, but is often encountered in case the hyperchromic-hypochromic toner system is applied carelessly in an easily fluctuating electrophotographic apparatus.

Therefore, in case of changing an input data Din from a minimum value to a maximum value for varying the gradation level from a minimum level to a maximum level (entire gradation levels), it is important to closely check the image quality utilizing the aforementioned image quality checking means in such a manner that the lightness L* of the patch image satisfies a relation:

$$L^*(Din1) > L^*(Din2)$$

in case Din1<Din2 and that, over the entire gradation levels (particularly in a state where the hyperchromic toner starts to be mixed in the hypochromic toner), a change $\Delta L^*$ in the lightness corresponding to 2% of the entire gradation levels is less than 10, preferably less than 5.

In the foregoing embodiments, the density detection of the patch image may be executed on the image bearing member (photosensitive member), on the intermediate transfer member, on the transfer material carrying member or on the transfer material such as a sheet. Also the density detection of the patch image on the transfer material may be made before or after the image fixation.

Also the control of the image forming condition on the transfer material, based on the result of the density detection of the patch image, may be made on at least one of the latent image forming condition, the developing condition, the transfer condition and the fixing condition.

Also the toner to which a hyperchromic toner and a hypochromic toner are to be applied is preferably at least one of magenta toner, cyan toner and yellow toner.

As explained in the foregoing, the present invention allows, in an image forming apparatus utilizing a hyperchromic toner and a hypochromic toner, to obtain an image excellent in gradation, without granularity even in an image area where the hypochromic toner and the hyperchromic toner are present mixedly, thereby enabling a smooth gradational presentation over the entire gradation range.

What is claimed is:

1. An image forming apparatus comprising:
   image forming means capable of forming an image with a hypochromic toner and a hyperchromic toner of a substantially same hue;
   a first toner containing portion containing said hypochromic toner;
   a second toner containing portion containing said hyperchromic toner; and
   density detecting means which detects a density of an image formed with said hypochromic toner and said hyperchromic toner.

2. An image forming apparatus according to claim 1, wherein said density detecting means detects a density of an image formed with said hypochromic toner.

3. An image forming apparatus according to claim 1, wherein said density detecting means detects a density of an image formed with said hyperchromic toner.

4. An image forming apparatus according to any of claims 1 to 3, wherein an image forming condition for an image to be formed by said image forming means on a transfer member is controlled according to a result of detection of said density detecting means.

5. An image forming apparatus according to claim 4, wherein, at an increase of gradation data for an image to be formed on said transfer member, said hypochromic toner is employed with an increasing recording rate while said hyperchromic toner is not employed until said gradation data reaches a predetermined value, and said hyperchromic toner is mixed, with an increasing recording rate, with said hypochromic toner beyond said predetermined value.

6. An image forming apparatus according to claim 1, wherein, in said image formed by said hypochromic toner and said hyperchromic toner and detected by said density detecting means, said hyperchromic toner has a recording rate smaller than a recording rate of said hypochromic toner.

7. An image forming apparatus according to claim 1, further comprising:
   an image bearing member;
   wherein said image detected by said density detecting means is formed on said image bearing member.

8. An image forming apparatus according to claim 1, further comprising:
an intermediate transfer member to which an image is transferred from an image bearing member;
wherein said image detected by said density detecting means is formed on said intermediate transfer member.

9. An image forming apparatus according to claim 4, wherein said image detected by said density detecting means is formed on said transfer member.

10. An image forming apparatus according to claim 9, wherein said density detecting means detects a density of said image fixed on said transfer member.

11. An image forming apparatus according to claim 4, wherein said image forming condition is at least one of a latent image forming condition, a developing condition, a transfer condition and a fixing condition.

12. An image forming apparatus according to claim 4, wherein, in case a result of detection of said density detecting means is not a desired value, said image forming condition is so controlled as to form an image with a proportion of the hypochromic toner and the hyperchromic toner, determined according to predetermined data indicating a relationship between gradation data and a toner proportion in an image.

13. An image forming apparatus according to claim 4, wherein, in case a result of detection of said density detecting means is not a desired value, a remaining amount of toner in at least one of said first toner containing portion and said second toner containing portion is brought to a predetermined amount.

14. An image forming apparatus according to claim 4, wherein, in changing an input data Din from a minimum value to a maximum value for varying the gradation level from a minimum level to a maximum level, said image forming condition is controlled in such a manner that a lightness L* of said image satisfies a relation:

$$L^*(Din1) > L^*(Din2)$$

in case Din1<Din2 and that a change ΔL* in the lightness corresponding to a change in said gradation data remains within a predetermined range.

15. An image forming apparatus according to claim 1, wherein said hypochromic toner and said hyperchromic toner has a color which is at least one of magenta, cyan and yellow.

16. An image forming apparatus comprising:
image forming means capable of forming an image with a hypochromic toner and a hyperchromic toner of a substantially same hue;
a first toner containing portion containing said hypochromic toner;
a second toner containing portion containing said hyperchromic toner; and
density detecting means which detects a density of a first image formed with said hypochromic toner and a density of a second image formed with said hyperchromic toner.

17. An image forming apparatus according to claim 16, wherein an image forming condition for an image to be formed by said image forming means on a transfer member is controlled according to a result of detection of said density detecting means.

18. An image forming apparatus according to claim 17, wherein, at an increase of gradation data for an image to be formed on said transfer member, said hypochromic toner is employed with an increasing recording rate while said hyperchromic toner is not employed until said gradation data reaches a predetermined value, and said hyperchromic toner is mixed, with an increasing recording rate, with said hypochromic toner beyond said predetermined value.

19. An image forming apparatus according to claim 16, further comprising:
an image bearing member,
wherein said image detected by said density detecting means is formed on said image bearing member.

20. An image forming apparatus according to claim 16, further comprising:
an intermediate transfer member to which an image is transferred from an image bearing member,
wherein said image detected by said density detecting means is formed on said intermediate transfer member.

21. An image forming apparatus according to claim 17, wherein said image detected by said density detecting means is formed on said transfer member.

22. An image forming apparatus according to claim 21, wherein said density detecting means detects a density of said image fixed on said transfer member.

23. An image forming apparatus according to claim 17, wherein said image forming condition is at least one of a latent image forming condition, a developing condition, a transfer condition and a fixing condition.

24. An image forming apparatus according to claim 17, wherein, in case a result of detection of said density detecting means is not a desired value, said image forming condition is so controlled as to form an image with a proportion of the hypochromic toner and the hyperchromic toner, determined according to predetermined data indicating a relationship between gradation data and a toner proportion in an image.

25. An image forming apparatus according to claim 17, wherein, in case a result of detection of said density detecting means is not a desired value, a remaining amount of toner in at least one of said first toner containing portion and said second toner containing portion is brought to a predetermined amount.

26. An image forming apparatus according to claim 17, wherein, in changing an input data Din from a minimum value to a maximum value for varying the gradation level from a minimum level to a maximum level, said image forming condition is controlled in such a manner that a lightness L* of said image satisfies a relation:

$$L^*(Din1) > L^*(Din2)$$

in case Din1<Din2 and that a change ΔL* in the lightness corresponding to a change in said gradation data remains within a predetermined range.

27. An image forming apparatus according to claim 16, wherein said hypochromic toner and said hyperchromic toner has a color which is at least one of magenta, cyan and yellow.

* * * * *

UNITED STATES PATENT AND TRADEMARK OFFICE
CERTIFICATE OF CORRECTION

PATENT NO. : 6,879,788 B2
DATED : April 12, 2005
INVENTOR(S) : Nobuyuki Ito et al.

It is certified that error appears in the above-identified patent and that said Letters Patent is hereby corrected as shown below:

Column 4,
Line 58, "(luminocity)," should read -- (luminosity), --; and
Line 62, "luminocity." should read -- luminosity. --.

Column 8,
Line 50, "toper" should read -- toner --.

Column 14,
Line 12, "luminocity," should read -- luminosity, --.

Column 18,
Line 59, "has" should read -- have --.

Signed and Sealed this

Thirtieth Day of August, 2005

JON W. DUDAS
*Director of the United States Patent and Trademark Office*